United States Patent
Márquez

(10) Patent No.: US 11,460,461 B2
(45) Date of Patent: Oct. 4, 2022

(54) METHOD FOR DETERMINING OIL CONCENTRATION IN WATER

(71) Applicant: YPF SOCIEDAD ANÓNIMA, Ciudad Autónoma de Buenos Aires (AR)

(72) Inventor: Francisco Manuel Márquez, Rada Tilly (AR)

(73) Assignee: YPF SOCIEDAD ANÓNIMA, Ciudad Autónoma de Buenos Aires (AR)

(*) Notice: Subject to any disclaimer, the term of this patent is extended or adjusted under 35 U.S.C. 154(b) by 260 days.

(21) Appl. No.: 16/851,757

(22) Filed: Apr. 17, 2020

(65) Prior Publication Data
US 2020/0378944 A1   Dec. 3, 2020

(51) Int. Cl.
*G01N 33/18* (2006.01)
*G01N 1/40* (2006.01)
*G01N 21/31* (2006.01)

(52) U.S. Cl.
CPC .......... *G01N 33/1833* (2013.01); *G01N 1/40* (2013.01); *G01N 21/31* (2013.01); *G01N 2001/4061* (2013.01)

(58) Field of Classification Search
CPC ............... G01N 33/1833; G01N 21/31; G01N 2001/4061
See application file for complete search history.

(56) References Cited

U.S. PATENT DOCUMENTS

| | | | |
|---|---|---|---|
| 2011/0292382 A1* | 12/2011 | Mostowfi | G01N 21/85 356/246 |
| 2015/0001384 A1 | 1/2015 | Szabo et al. | |
| 2015/0021490 A1* | 1/2015 | Han | G01N 33/1833 250/372 |
| 2015/0106034 A1 | 4/2015 | Koseoglu et al. | |

FOREIGN PATENT DOCUMENTS

| | | | | |
|---|---|---|---|---|
| AU | 2013234794 A1 * | 11/2014 | | C02F 1/008 |
| CN | 106644980 A | 5/2017 | | |
| CN | 109030397 A * | 12/2018 | | G01N 21/33 |
| CN | 112485211 A * | 3/2021 | | |
| WO | WO-2007089154 A1 * | 8/2007 | | G01N 21/3577 |

* cited by examiner

*Primary Examiner* — Maurice C Smith
(74) *Attorney, Agent, or Firm* — Muncy, Geissler, Olds & Lowe, P.C.

(57) ABSTRACT

A molecular spectrophotometric method of high precision and accuracy for determining concentration of oil-derived hydrocarbons in water is described. The method allows to obtain direct measurements of oil mass concentration in a water sample and uses environmentally friendly solvents.

10 Claims, 2 Drawing Sheets

METHOD FOR DETERMINING OIL CONCENTRATION IN WATER

FIELD OF THE INVENTION

The present invention refers to the technical field of determination of oil concentration in water. In particular, the present invention refers to a molecular spectrophotometric method for determining the concentration of oil-derived hydrocarbons in water using non-halogenated solvents, that may be applied in oil recovery processes.

BACKGROUND OF THE INVENTION

Determination of oil concentration in water is of interest for assessing assisted and enhanced oil recovery processes, as well as for the engineering of remediation operations for hydrocarbon-polluted soil or groundwaters.

The oil mass concentration value is of particular interest, as it allows calculations based on matter balances, without the need to resort to empirical expressions for density or to complex mathematical models, for example based on activity coefficients, to obtain the oil mass in a sample from its volumetric fraction or concentration.

There are several methods available in the prior art for quantifying petroleum in an aqueous sample. Such methods may be based on a visual estimate or use instruments available in a laboratory, such as methods based on near infrared spectroscopy, nuclear magnetic resonance, or absorption spectroscopy.

U.S. patent application No. 2015/0001384 relates to a method for quantifying organic matter, such as oil, in a sample, using a UV-visible spectrophotometer. The described method does not allow direct obtention of oil mass concentration in a water sample, as the obtention of calibration curves is not obtained.

U.S. patent application No. 2015/0021490 describes a method for determining oil traces in water that comprises developing a calibration curve, as well as extracting oil from a sample using toluene. The described method allows to obtain the volumetric fraction of oil in an oil and water sample, from a volumetric calibration curve.

Patent application CN 106644980 describes a method for detecting oil in residual waters from a calibration curve developed using oil-in-water solutions. Results thus obtained are of low accuracy and precision due to inconveniences associated with handling biphasic solutions, as are oil-in-water solutions.

The EPA 418.1 method, widely used in the oil industry, allows to quantify oil in water using a method based on infrared spectroscopy with a 1 mg/L precision. The method uses solvents that are harmful for the environment such as halogenated hydrocarbons.

None of the prior art documents describe methods that allowed to obtain an oil mass concentration value in a water sample with high precision and accuracy.

Thus there is a need to provide a method for determining oil concentration in water that allows to obtain oil mass concentration in a water sample directly and with higher precision and accuracy compared to prior art methods, and which can be used with environmentally friendly solvents.

BRIEF DESCRIPTION OF THE INVENTION

Thus, an object of the present invention a method for determining oil concentration in water comprising the steps of:

a) providing a stock solution comprising dehydrated oil and an organic solvent;
b) preparing a plurality of calibration solutions from mass dilutions of said stock solution using said organic solvent, wherein each one of the plurality of calibration solutions has a dehydrated oil concentration in said organic solvent;
c) measuring absorbance corresponding to each of said plurality of calibration solutions;
d) obtaining a mass calibration curve from the absorbances of each one of the plurality of calibration solutions measured in step c) and of the oil-in-water concentrations corresponding to each of said plurality of calibration solutions;
e) providing a sample comprising oil and water;
f) extracting oil from said sample using said organic solvent;
g) measuring absorbance of oil dissolved in said organic solvent, extracted from said sample in step f); and
h) determining oil concentration in water in the sample from the absorbance measured in step g) and the mass calibration curve developed in step d).

In a preferred embodiment of the method of the present invention, the step b) of preparing a plurality of calibration solutions from dilutions of a stock solution with said organic solvent comprises, for each one of the plurality of calibration solutions, the steps of:

i) determining an approximate volume of stock solution to prepare the calibration solution,
ii) introducing said approximate volume of stock solution in a container comprising said organic solvent and weighing the mass of stock solution effectively introduced in the container with an analytical balance, y
iii) calculating oil concentration in water corresponding to the calibration solution from the mass of stock solution weighed in ii).

In a more preferred embodiment, the step i) of determining an approximate volume of stock solution to prepare the calibration solution comprises determining the density of the stock solution.

In a more preferred embodiment of the method of the present invention, the step iii) of calculating oil concentration in water corresponding to the calibration solution comprises the use of a correlation factor between oil concentration in the organic solvent and oil concentration in water.

In an even more preferred embodiment of the method of the present invention, the approximate volume of stock solution $V_{S_i}$ to prepare a calibration solution i of an approximate concentration $c'_i$ is calculated according to equations (1) and (2):

$$m'_{S_i} = \frac{\phi c'_i V_i \rho_S}{c_S} \quad (1)$$

$$V_{S_i} = \frac{m'_{S_i}}{\rho_S} \quad (2)$$

$\phi$ being a correlation factor, $\rho_S$ being the density of the stock solution, $V_i$ being the volume of the calibration solution i, and concentration $c_i$ of the calibration solution i is calculated according to the equation (3):

$$c_i = \frac{m_{S_i} c_S}{\phi \rho_S V_i} \quad (3)$$

wherein i=1, 2, ..., N, with N being the number of points in the mass calibration curve.

In a preferred embodiment of the method of the present invention, the step f) of extracting oil from said sample of oil in water using said organic solvent comprises the steps of:
i. providing a volume of an oil in water sample;
ii. contacting said volume of an oil in water sample with a volume of organic solvent;
wherein the ratio between said volume of oil in water sample and said volume of organic solvent is equal to the correlation factor between oil concentration in the organic solvent and oil concentration in water.

In a preferred embodiment of the method of the present invention, absorbance measurements are performed using a spectrophotometer. Preferably, absorbance measurements are performed at a 450 nm wavelength.

In another preferred embodiment of the method of the present invention, the organic solvent is an organic solvent which does not contain chlorine and does not absorb electromagnetic radiation at a wavelength between 340 nm and 700 nm. Preferably, the organic solvent is selected from cyclohexane, kerosene, or combinations thereof.

DETAILED DESCRIPTION OF THE INVENTION

Figure 1:
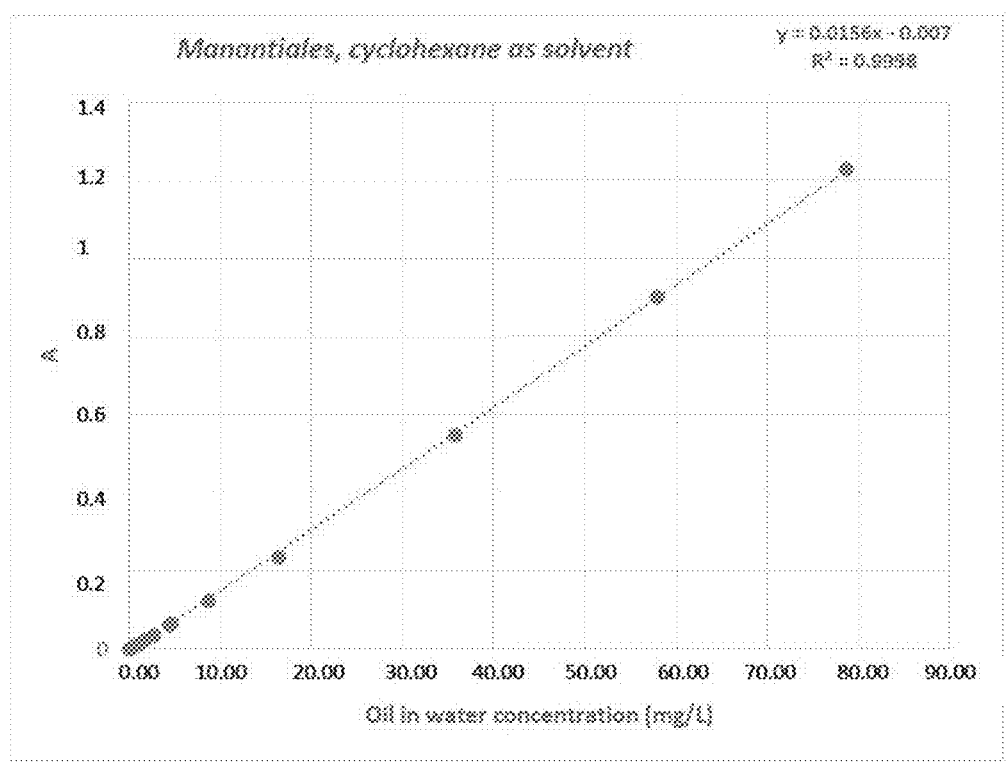
FIG. 1 shows the mass calibration curve obtained in the method of the present invention in an oil in water sample from the Manantiales Behr deposit, in the province of Chubut, Argentina, using cyclohexane as organic solvent.

The invention will be described in greater detail hereinbelow, with reference to the figures and exemplary embodiments.

As used herein, the term "spectrophotometer" is used to refer to instruments that allow to determine absorbance (A) or transmittance (T) of a solution contained in a measurement cell. "Absorbance" or "transmittance" refer to several variables that may be measured related to absorptivity or transmissibility, respectively, of a substance, physical properties defined respectively as the fraction of electromagnetic radiation that is absorbed or transmitted by said substance at a determined wavelength. Absorbance of a substance, as measured by a spectrophotometer, is related to the concentration of said substance in said solution according to Beer-Lambert law:

$$A = l\varepsilon c$$

A being the absorbance of the sample, l being the optical path of the radiation that goes through the cell, $\varepsilon$ being absorptivity and c being the concentration of the substance in the solution.

Thus, a molecular absorption spectrophotometer, such as an spectrophotometer operating in wavelengths corresponding to the UV or visible regions of the electromagnetic radiation spectrum, allow to determine concentrations of substances that possess a specific absorption at a determined wavelength, thus making it possible to develop the mass calibration curve as will be further described herein.

As used herein, the expression "mass dilution" refers to the dilution of a solution obtained considering the mass of a determined compound and not its volume. In the context of the present invention, said mass dilution is obtained considering oil mass.

As used herein, the expression "correlation factor" refers to an empiric relation between physical variables. In the context of the present invention, correlation factor is used to relate oil concentration in water to oil concentration in an organic solvent, as well as the volume of organic solvent to be used for extracting oil at the volume of a mixture comprising oil and water, from which oil is extracted.

The first step of the method of the present invention consists in preparing an oil stock solution in an organic solvent. To this end, a 100.0 ml flask, perfectly clean and dry, is used. Said flask is placed, without a lid, on an analytical balance, which is tared (that is, set to a zero weight). Then, approximately 0.2000 g of dehydrated oil are weighed on said balance, taken with and deposited within the flask using a syringe. The value of oil mass weighed by the analytical balance must be recorded. Said value need not be exactly 0.2000 g, instead, the value of dehydrated oil mass must be exactly recorded.

Then, using a glass beaker, the organic solvent is added to the flask which contains the weighted oil mass. The solvent is added until the flask is flush, wherein this may be done with a Pasteur glass pipette, or a similar device.

The uncapped flask is weighed again on the analytical balance, and the value of the mass of the stock solution to be used to determine the density of the stock solution is recorded, expressed for example in mg of oil/ml of solvent, as shown below. Since this value is relevant for the preparation of subsequent dilutions, the flask must not be contaminated on the outside before determining the weight of the solution. Thus, it is advisable to use suitable equipment, such as gloves, and to clean the outer surface of the flask with absorbent paper. Once the weighing is completed and the mass values have been recorded, the flask lid is placed and the solution is homogenized, for example by inverting the flask several times.

To prepare the different points of the mass calibration curve, calibration solutions corresponding to different levels of oil concentration in water are prepared, the flasks and their respective lids are washed three times with the selected organic solvent. A certain amount of organic solvent is left inside each flask, for example approximately ¼ of its respective volume, in order to avoid the evaporation of the stock solution that would take place if it were added directly to the glass of the flask. Once the flasks are ready to be used for the mass calibration curve, the stock solution is loaded into a 10 ml disposable syringe. Said syringe is placed on the analytical balance in reverse and the balance is then tared. For each of the flasks thus prepared, a certain volume of stock solution, corresponding to a point on the mass calibration curve, is added using the syringe. Once this volume of stock solution has been added, the emptied syringe is weighed again on the balance, recording the new weight value obtained, so that the mass of stock solution introduced into the flask for the preparation of the calibration solution can be calculated. The rest of the organic solvent is added to the flask to bring it up to volume, washing the neck of the flask with said organic solvent. The flask should not be capped until it is flush, as there may be stock solution left on the walls. Once it is flush, the flask is shaken several times to homogenize the solution. Meanwhile, the syringe is tared again, and this procedure is repeated with successive dilutions. If for the upper points of the curve it is necessary to load the syringe more than once, it is advisable to transfer the stock solution to a glass container, such as a small beaker. Additionally, it is advisable not to leave the syringe with less than 2 ml of stock solution inside, since if the volume is lower, evaporation of the stock solution will occur rapidly, making it difficult to obtain a stable weight determination.

Once the calibration solutions have been prepared, absorbances are read with a spectrophotometer. First, the measurement cell is loaded with the solvent used, after having washed the cell with the solvent three times, and the reading of the spectrophotometer is recorded at a 450 nm wavelength, corresponding to a zero oil-in-water concentration. Then, the curve is measured from the most diluted point towards the most concentrated one, washing the cell three times with the solution to be measured before recording the value of the measured absorbance.

The mass calibration curve will be developed from pairs $\{c_i, A_i\}$, $c_i$ being oil concentration in water of the calibration solution i and $A_i$ being the corresponding measured absorbance, wherein i=1, 2, . . . , N where N is the number of desired points on the mass calibration curve with a concentration different from zero, corresponding to the number of solutions prepared from the stock solution as mentioned above.

Since the calibration solutions have different concentrations of oil in an organic solvent, it is necessary to have a correlation between oil concentration in organic solvent and oil concentration in water for each of the points in the mass calibration curve. This correlation allows a direct reading of results in appropriate units for determining mass concentration of oil in water.

In order to obtain such correlation and determine concentration $c_i$ in units of oil mass/water volume, such as mg/L, corresponding to the calibration solution represented by point i of the curve, an estimated stock solution weight is calculated to prepare the calibration solution corresponding to said point, and then said value is recalculated based on the value actually weighed and recorded.

Density of the stock solution, in mg/L, may be calculated according to equation (1):

$$\rho_S = \frac{m_S}{V_0} \quad (1)$$

$m_S$ being the mass of stock solution weighed, in mg, and $V_0$ being the volume of solution in the flask containing the stock solution, in L.

Concentration of the stock solution, in mg of oil/L of stock solution, is calculated according to equation (2):

$$c_S = \frac{m_{PD}}{V_0} \quad (2)$$

$m_{PD}$ being the mass of dehydrated oil weighed for the preparation of the stock solution, in mg.

For the preparation of point i of the mass calibration curve, corresponding to an oil concentration in water $c_i$, approximately one mass of stock solution as given by the equation (3) must be added to the flask i:

$$m'_{S_i} = \frac{\phi c'_i V_i \rho_S}{c_S} \quad (3)$$

$\phi$ being the correlation factor dependent on the chosen organic solvent, $c'_i$ being the approximate oil concentration in water that will represent point i, and $V_i$ being the volume of calibration solution in the flask corresponding to point i. The corresponding volume of stock solution to be added to the flask in order to prepare the calibration solution, for example, using the syringe as described above, may be estimated using the density of the stock solution and equation (4):

$$V_{S_i} = \frac{m'_{S_i}}{\rho_S} \quad (4)$$

The value of oil concentration in water $c_i$ which represents this point in the curve must be recalculated using the mass effectively added, using equation (5):

$$c_i = \frac{m_{S_i} c_S}{\phi \rho_S V_i} \quad (5)$$

$m_{S_i}$ being the mass of solution actually added, obtained by weighing the syringe after adding the volume of stock solution, as indicated before.

Thus, each point of the mass calibration curve, with an absorbance $A_i$ corresponding to a determined oil concentration in the organic solvent, may be correlated to a determined oil concentration in water using equation (3).

After that, the mass calibration curve will be given by the geometrical place of the pair set $\{c_i, A_i\}$, wherein i=1, 2, . . . , N. Lineal regression techniques may also be used, such as a least squares method.

In order to analyze a sample comprising oil and water using the developed mass calibration curve, a process of extraction of the organic phase or "clean up" (cleaning the sample) must be previously performed, and afterwards, the absorbance of the organic phase thus extracted must be measured.

For this process, it is necessary to perform an extraction using a volume of organic solvent $V_S$ such that equation (6) is true $$V_S \phi^{-1} V_M \quad (6)$$

$V_M$ being the volume of the sample to analyze.

Once absorbance of the sample $A_M$ has been measured, the corresponding value of oil concentration in water will be obtained using the mass calibration curve previously developed.

The value of the correlation factor used in the method of the present invention is a function of the organic solvent used. Particularly, its value will be related to solubility of oil in water and in the organic solvent. The value of the correlation factor may be between 1 and 20. Typically, a value of 10 may be used in the method of the present invention when the organic solvent is immiscible in water, such as cyclohexane or kerosene.

The method of the present invention allows to obtain highly precise and accurate results, while providing reduced response times and more reliable results compared to methods of the prior art.

The method of the present invention allows to directly obtain oil concentration in water, expressed as mass/unit of volume, from spectrophotometric measurements, unlike prior art methods whereby only volumetric concentration may be obtained and further calculations are required to determine the associated oil mass.

The method of the present invention may be carried out with a wide variety of instruments typically available in analysis laboratories, thus allowing to reduce variability of results among laboratories due to differences in measuring instruments or to the use of different organic solvents to determine absorbance.

EXAMPLES

Figure 2:
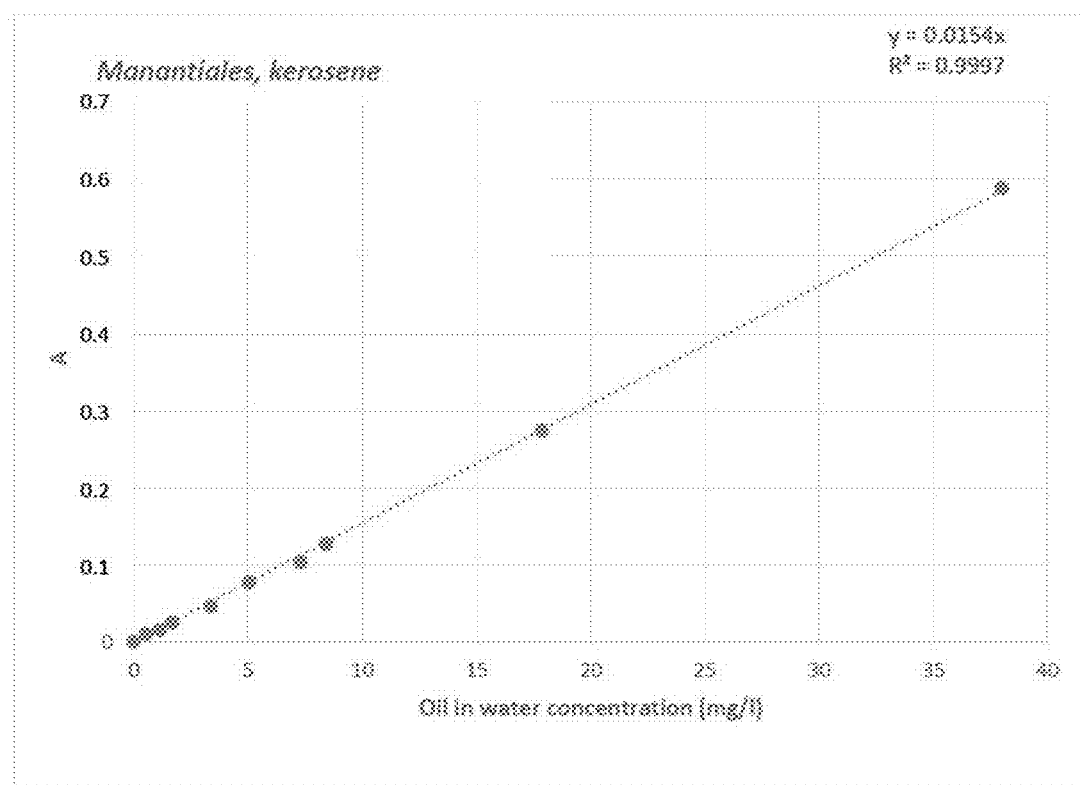
FIG. 2 shows the mass calibration curve obtained in the method of the present invention in an oil in water sample from the Manantiales Behr deposit, in the province of Chubut, Argentina, using kerosene as organic solvent.

The method of the present invention was used to determine oil concentration in water from samples from different sources. The obtained calibration curves may be observed in FIGS. 1 and 2. High lineal correlation coefficients, of a value close to a unit, are observed.

In order to show the remarkable improvements in precision and accuracy that may be achieved through the method of the present invention, comparative assays were performed using a prior art method wherein calibration solutions where prepared using volumetric pipettes.

Precision

The precision of the calibration method by standards weighing allows obtaining an increase in precision of almost two orders of magnitude. Thus, while the volumetric methods of the prior art possess accuracies of about ±0.02 mg/L, the method of the present invention possesses an accuracy of about ±0.0002 mg/L.

The results of comparative measurements are presented in the tables below. Variability of the results measured with prior art methods can be observed, as well as the precision obtained by successive replications of the measurements. Improvements of about 100% are observed in accuracy.

TABLE 1

| Comparative assay no1 | | |
| --- | --- | --- |
| Measurement | Prior art (mg/L) | Invention (mg/L) |
| 1 | 0.3 | 0.261 |
| 2 | 0.4 | 0.262 |
| 3 | 0.2 | 0.260 |
| 4 | 0.2 | 0.263 |
| 5 | 0.3 | 0.260 |
| Average | 0.28 | 0.2612 |
| Dilution | 0 | 0 |
| Standard deviation | 0.084 | 0.001 |
| Improvement in precision | | 98% |

TABLE 2

| Comparative assay no2 | | |
| --- | --- | --- |
| Measurement | Prior art (mg/L) | Invention (mg/L) |
| 1 | 0.6 | 0.554 |
| 2 | 0.5 | 0.551 |
| 3 | 0.8 | 0.556 |
| 4 | 0.5 | 0.554 |
| 5 | 0.6 | 0.553 |
| Average | 0.6 | 0.5536 |
| Dilution | 0 | 0 |
| STD dev | 0.122 | 0.002 |
| Improvement in precision | | 99% |

TABLE 3

| Comparative assay no3 | | |
| --- | --- | --- |
| Measurement | Prior art (mg/L) | Invention (mg/L) |
| 1 | 5.2 | 5.023 |
| 2 | 5.4 | 5.027 |
| 3 | 4.9 | 5.018 |
| 4 | 5.8 | 5.02 |
| 5 | 5.5 | 5.024 |
| Average | 5.36 | 5.0224 |
| Dilution | 0 | 0 |
| STD dev | 0.336 | 0.004 |
| Improvement in precision | | 99% |

TABLE 4

| Comparative assay no4 | | |
| --- | --- | --- |
| Measurement | Prior art (mg/L) | Invention (mg/L) |
| 1 | 20.6 | 20.044 |
| 2 | 22.4 | 20.167 |
| 3 | 21.7 | 20.08 |
| 4 | 23.5 | 20.158 |
| 5 | 22.7 | 20.071 |
| Average | 22.18 | 20.104 |
| Dilution | 10 | 10 |
| STD dev | 1.094 | 0.055 |
| Improvement in precision | | 95% |

Accuracy

Accuracy of the method was assessed preparing a solution of a known concentration of oil in cyclohexane. Said concentration was determined using a prior art method and the method of the present invention. Remarkable improvements in accuracy of the method are observed.

TABLE 5

| Comparative assay no5 | | |
| --- | --- | --- |
| Added value (mg) | Prior art (mg/L) | Invention (mg/L) |
| 0.5234 | 0.6 | 0.521 |
| 1.0204 | 1.2 | 1.025 |
| 5.2205 | 4.4 | 5.270 |
| 10.3411 | 13.6 | 10.559 |
| 20.1477 | 26.2 | 20.588 |

Organic Solvent

Spectral scans were performed with different organic solvents to extract the oil from the samples in order to determine the optimal wavelength for absorbance measurements. Organic solvents of the present invention must be insoluble in water and must meet the condition of having the lowest possible absorbance at the wavelength of analysis of 450 nm, so as to optimize the accuracy and precision of the method. Spectral scanning is performed from 340 nm to 700 nm.

The method of the present invention can be used with a wide variety of hydrocarbon-based solvents, such as cyclohexane, cyclopentane and kerosene. Preferably, the solvent used has a reduced environmental impact compared to the solvents traditionally used in the prior art methods.

Using this technique of spectral scanning solvents that are more environmentally friendly, it is possible to select those that, having a low water solubility, present the least possible absorbance in the working wavelength of 450 nm, in the area corresponding to the visible spectrum of electromagnetic radiation.

The invention claimed is:

1. A method for determining oil concentration in water, the method comprising the steps of:
   a) providing a stock solution comprising dehydrated oil and an organic solvent;
   b) preparing a plurality of calibration solutions from mass dilutions of said stock solution using said organic solvent, wherein each one of the plurality of calibration solutions has a dehydrated oil concentration in said organic solvent;
   c) measuring absorbance corresponding to each of said plurality of calibration solutions;
   d) obtaining a mass calibration curve from the absorbances of each one of the plurality of calibration solutions measured in step c) and of the oil-in-water concentrations corresponding to each of said plurality of calibration solutions;
   e) providing a sample comprising oil and water;
   f) extracting oil from said sample using said organic solvent;
   g) measuring absorbance of oil dissolved in said organic solvent, extracted from said sample in step f); and
   h) determining oil concentration in water of the sample from the absorbance measured in step g) and of the mass calibration curve developed in step d).

2. The method according to claim 1, wherein the step b) of preparing a plurality of calibration solutions from dilutions of a stock solution with said organic solvent comprises, for each one of the plurality of calibration solutions, the steps of:
   i) determining an approximate volume of stock solution to prepare the calibration solution,
   ii) introducing said approximate volume of stock solution in a container comprising said organic solvent and weighing the mass of stock solution effectively introduced in the container with an analytical balance, and
   iii) calculating oil concentration in water corresponding to the calibration solution from the mass of stock solution weighed in ii).

3. The method according to claim 2, wherein the step i) of determining an approximate volume of stock solution to prepare the calibration solution comprises determining the density of the stock solution.

4. The method according to claim 3, wherein the step iii) of calculating oil concentration in water corresponding to the calibration solution comprises the use of a correlation factor between oil concentration in the organic solvent land the oil concentration in water.

5. The method according to claim 4, wherein the approximate volume of stock solution $V_{S_i}$ to prepare a calibration solution i corresponding to an approximate concentration $c'_i$ is calculated according to equations (1) and (2):

$$m'_{S_i} = \frac{\phi c'_i V_i \rho_S}{c_S} \quad (1)$$

$$V_{S_i} = \frac{m'_{S_i}}{\rho_S} \quad (2)$$

$\phi$ being the correlation factor, $p_s$ being the density of the la stock solution, $V_i$ being the volume of the calibration solution i, and concentration $c_i$ corresponding to the calibration solution i is calculated according to equation (3):

$$c_i = \frac{m_{S_i} c_S}{\phi \rho_S V_i} \quad (3)$$

wherein i=1,2, . . . ,N, with N being the number of points in the mass calibration curve.

6. The method according to claim 5, wherein the step f) of extracting oil from said sample of oil in water using said organic solvent comprises the steps of:
   i. providing a volume of an oil in water sample;
   ii. contacting said volume of an oil in water sample with a volume of organic solvent;
   wherein the ratio between said volume of oil in water sample y said volume of organic solvent is equal to the correlation factor between oil concentration in the organic solvent and oil concentration in water.

7. The method according to claim 1, wherein absorbance measurements are performed using a spectrophotometer.

8. The method according to claim 7, wherein absorbance measurements are performed at a wavelength of 450 nm.

9. The method according to claim 8, wherein the organic solvent is an organic solvent that does not contain chlorine and does not absorb electromagnetic radiation at a wavelength of between 340 nm and 700 nm.

10. The method according to claim 9, wherein the organic solvent is selected from cyclohexane, kerosene, or combinations thereof.

* * * * *